(12) United States Patent
Dubois et al.

(10) Patent No.: US 7,480,574 B2
(45) Date of Patent: Jan. 20, 2009

(54) METHOD TO CHARACTERIZE MATERIAL USING MATHEMATICAL PROPAGATION MODELS AND ULTRASONIC SIGNAL

(75) Inventors: Marc Dubois, Clifton Park, NY (US); Peter W. Lorraine, Nishayana, NY (US); Robert J. Filkins, Nishayana, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/975,560

(22) Filed: Oct. 28, 2004

(65) Prior Publication Data

US 2005/0102109 A1    May 12, 2005

Related U.S. Application Data

(62) Division of application No. 09/996,098, filed on Nov. 26, 2001, now Pat. No. 6,856,918.

(51) Int. Cl.
*G06F 19/00* (2006.01)
(52) U.S. Cl. .............................. 702/39; 702/38; 702/40; 73/598; 73/602; 73/624; 73/600; 73/627; 73/544; 73/599; 356/432; 356/381
(58) Field of Classification Search ............. 702/38–40; 73/598, 602, 624, 600, 627, 644, 599; 356/432, 356/381
See application file for complete search history.

(56) References Cited

U.S. PATENT DOCUMENTS

| | | | | | |
|---|---|---|---|---|---|
| 4,662,222 | A | * | 5/1987 | Johnson | 73/602 |
| 5,115,681 | A | * | 5/1992 | Bouheraoua et al. | 73/801 |
| 5,253,530 | A | * | 10/1993 | Letcher, III | 73/602 |
| 5,274,607 | A | * | 12/1993 | Bean | 367/98 |
| 5,677,489 | A | * | 10/1997 | Spillman, Jr. | 73/598 |
| 6,256,100 | B1 | * | 7/2001 | Banet et al. | 356/432 |

* cited by examiner

*Primary Examiner*—Tung S Lau
*Assistant Examiner*—Sujoy K Kundu
(74) *Attorney, Agent, or Firm*—Bracewell & Giuliani LLP

(57) ABSTRACT

The invention is directed to a system and method for detecting defects in a manufactured object. These defects may include flaws, delaminations, voids, fractures, fissures, or cracks, among others. The system utilizes an ultrasound measurement system, a signal analyzer and an expected result. The signal analyzer compares the signal from the measurement system to the expected result. The analysis may detect a defect or measure an attribute of the manufactured object. Further, the analysis may be displayed or represented. In addition, the expected result may be generated from a model such as a wave propagation model. One embodiment of the invention is a laser ultrasound detection system in which a laser is used to generate an ultrasonic signal. The signal analyzer compares the measured ultrasonic signal to an expected result. This expected result is generated from a wave propagation model. The analysis is then displayed on a monitor.

27 Claims, 11 Drawing Sheets

METHOD TO CHARACTERIZE MATERIAL USING MATHEMATICAL PROPAGATION MODELS AND ULTRASONIC SIGNAL

CROSS-REFERENCE TO RELATED APPLICATION

This application is a divisional of and claims the benefit of priority to U.S. patent application Ser. No. 09/996,098, U.S. Pat. No. 6,856,918, entitled "Method to Characterize Material Using Mathematical Propagation Models and Ultrasonic Signal", filed on Nov. 26, 2001, and is incorporated herein by reference in its entirety.

BACKGROUND

1. Field of the Invention

The present invention generally relates to a method to characterize a material using ultrasound measuring devices. In particular, the present invention relates to detecting defects in a material by comparing the results of a mathematical model and an ultrasonic signal emitted during laser ultrasound testing.

2. Description of Prior Art

Ultrasound testing methods are non-invasive, generally non-destructive, techniques used to measure features of materials. These features may include layer thickness, cracks, delamination, voids, disbonds, foreign inclusions, fiber fractions, fiber orientation, and porosity. The features may influence a given material's qualities and performance in given applications. Each application places unique demands on the material's qualities including the need for differing strength, flexibility, thermal properties, cost, or ultraviolet radiation resistance. With the changing demands, more non-invasive, non-destructive testing of materials is being performed using techniques such as ultrasound testing.

Ultrasound testing includes transducer-induced, laser and plasma-initiated ultrasound. Transducer-induced ultrasound techniques use piezoelectric transducers to induce an ultrasonic signal in an object.

Laser ultrasound techniques use a laser pulse. When the laser pulse is directed at an object, it causes thermal expansion in a small region. This thermal expansion causes ultrasonic waves. These ultrasonic waves are then measured by a detector and converted into information about the features of the object. The laser pulse may be generated by several lasers including a ruby laser, a carbon laser, and a Nd:YAG laser.

In some cases, a higher laser-energy density can be used and some matter at the material surface is ablated. The recoil effect of the pulverized matter launches ultrasonic waves in the material. Similarly to the thermoelastic regime, this ablation regime produces ultrasonic waves that can be detected and converted into information about the features of the object.

Similar to the laser ultrasound, plasma-induced ultrasound causes thermal expansion initiated ultrasonic waves. Often, a laser generates the plasma by directing a pulse at a false target in proximity to the manufactured object. The plasma then hits the manufactured object, producing an ultrasonic wave.

The manufactured object may be composed of different materials including metal, polymer, composite, or ceramic materials. The detector may be one of several devices. For example, the detector may be a transducer on the surface of the object, a laser interferometer directed at the object, or a gas-coupled laser acoustic detector, to name a few.

Ultrasound techniques are applied in research as well as industrial settings. In research, ultrasound techniques are used to test new materials for desired features. The technique is used to seek defects in material that has undergone stress or environmental endurance testing. In an industrial setting, the technique is used during scheduled servicing or during manufacturing to inspect parts for defects. Aircraft, automobile and other commercial industries have shown increasing interest in these techniques.

However, one difficulty associated with ultrasound techniques is found in discerning information about the features of the object from the measured ultrasonic waves. Many of the objects are constructed from composite materials with multiple layers. As the waves traverse the material, they reflect off interfaces or defects, propagate at differing speeds within different layers and change amplitude. The measured signal is a complex compilation of these reflections, ultrasonic velocity differences and amplitude changes. More layers and differing materials add to the complexity. In general, an expert is required to discern relevant aspects of the complex ultrasound signal.

One approach used by experts is to determine which peaks within the signal signify a reflection off of the back surface of the object. The expert then looks for smaller peaks between the back surface reflection peaks to determine number of layers or other structural features. The distance between smaller peaks or the amplitude of these peaks yields information about the thickness of a layer, the composition of the layer, or the interface between layers.

By implication, ultrasound techniques require a great deal of expertise. This requirement limits the broad application of ultrasonic techniques in industrial settings and makes the technique expensive. Another problem is the amount of time associated with translating an ultrasound signal into understandable information about the features within the object. Long translation times lead to expensive labor costs and reduced numbers of tests.

As such, many ultrasound techniques suffer from difficulties associated with translating complex ultrasound signals. Many other problems and disadvantages of the prior art will become apparent to one skilled in the art after comparing such prior art with the present invention as described herein.

SUMMARY OF THE INVENTION

Aspects of the invention are found in a system and method for detecting a physical attribute of a manufactured object. The system includes an ultrasound testing device, a signal analyzer, and an expected result. The signal analyzer is coupled to the ultrasound testing device. In operation, the ultrasound measuring device detects a signal indicative of the manufactured object. The ultrasound measuring device generates a measured signal. Further, the signal analyzer compares the measured signal to the expected result.

Other aspects may be included on an as needed basis. For example, a model processor may be included to generate the expected result. A model processor may, for example, be a computer programmed with a mathematical model of ultrasound propagation. The expected result may, for example, be calculated using an ultrasonic propagation mathematical model and the expected characteristics of the manufactured object.

Further, a representation of the manufactured object may be included. The model processor may generate the expected result from the representation of the manufactured object. In a further example, the representation of the manufactured object may be a computer-aided-design (CAD) representation of the manufactured object.

Further, the model processor may, using the mathematical model, extract the relevant information from the ultrasonic signal with or without a-priori knowledge of the manufactured object. As an example, the model processor may extract from the ultrasonic signal the number of layers and the position of a defect in the manufactured object. One exemplary method for obtaining the relevant information is to generate an expected ultrasonic signal using a propagation model that approximates a measured experimental signal. By manipulating parameters of the propagation model, the output from the propagation model nearly approximates the measured signal. The parameters used in matching the measured experimental signal are then indicative of the manufactured object. As such, the model parameters may be used to plot representations of the manufactured object. Additionally, they may be compared to an acceptable range of parameters. If the value of the parameters is outside that range, a defect is detected.

A programmable circuitry may also be connected to the model processor. The model processor may generate the expected result with the programmable circuitry.

Another aspect of the invention is the signal analyzer. The signal analyzer compares a measured result to an expected result. In this manner, the signal analyzer detects the physical attribute of the manufactured object. Further, the signal analyzer may detect the physical attribute of the manufactured object with respect to a model representation.

As such, a system and method for detecting a physical attribute in a manufactured object is described. Other aspects, advantages and novel features of the present invention will become apparent from the detailed description of the invention when considered in conjunction with the accompanying drawings.

DETAILED DESCRIPTION OF THE PREFERRED EMBODIMENT

Figure 1:
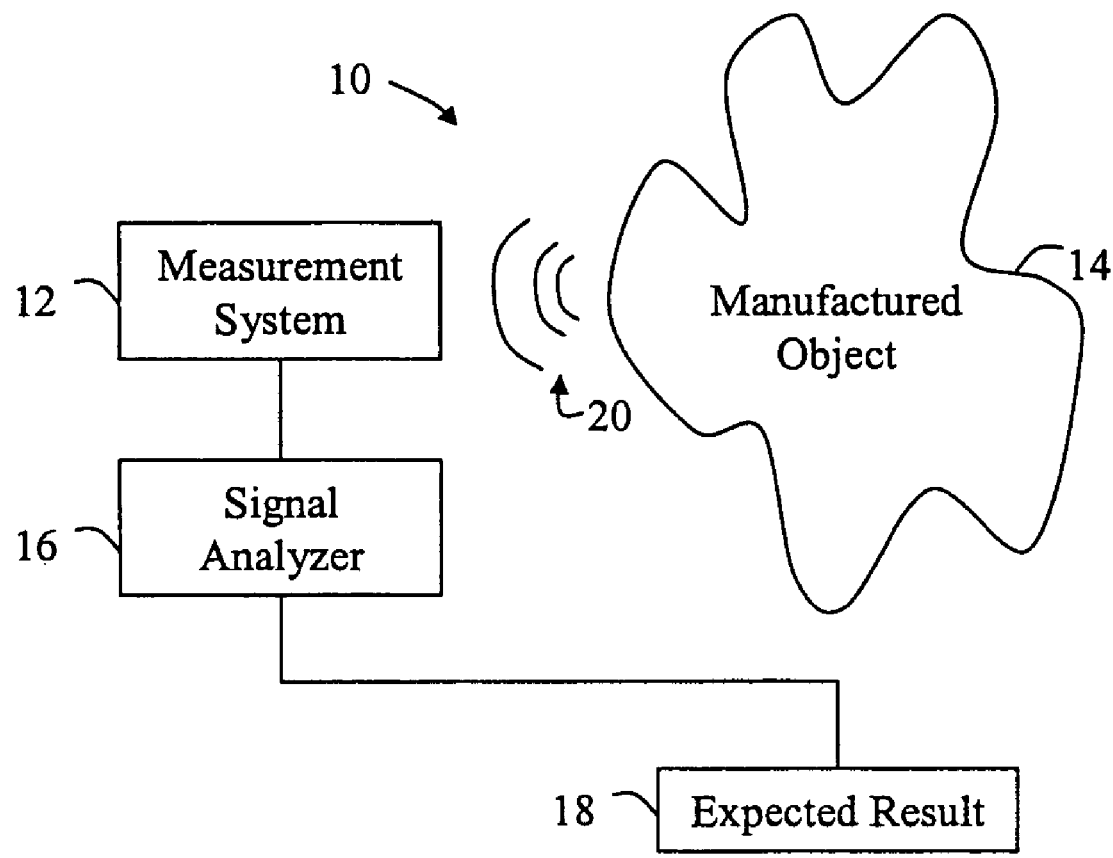
FIG. 1 is a schematic block diagram of a system for detecting physical attributes of a manufactured object according to the invention.

FIG. 1 is a schematic block diagram of a system for detecting physical attributes of a manufactured object 14 according to the invention. As depicted, the system 10 has a measurement system 12, a signal analyzer 16, and an expected result 18. The signal analyzer 16 is coupled to the measurement system 12. The expected result 18 is in communication with the signal analyzer 16. In practice, the signal analyzer, measurement system and the expected result may be encompassed in the same apparatus, separately housed, or constructed in various combinations.

The measurement system 12 detects a sonic energy signal 20 in the manufactured object 16. Then, the signal analyzer 16 receives the signal and automatically compares the signal to the expected result 18. By comparing the signal and the expected result 18, the signal analyzer 16 may detect the physical attribute of the manufactured object 14. Further, this comparison may be iterative wherein the signal is compared to a plurality of expected results 18 and/or an adjusted expected result 18.

The measurement system 12 may use various means for detecting the sonic energy signal 20. These means may include one or more piezoelectric transducers, one or more electromagnetic transducers, a laser interferometer, or a gas-coupled laser acoustic detector, to name a few.

The signal analyzer 16 may manipulate the measured signal and expected result 18 in various ways. These manipulations may include a simple subtraction of the expected result 18 from the signal, transformation of the time domain signal into a frequency domain, or filtering the signal, among others.

The analysis of the signal may also be performed in several ways. For example, an expert system may pick relevant amplitude peaks in the signal. The analysis may also include comparisons between a frequency domain transformation of the signal and the expected result 18. Additionally, the analysis may identify peaks, measure time differences between peaks, watch for missing peaks, or other analysis activities. Each of these activities may be automated. Further, the analysis may involve comparing the signal in one of many forms to a plurality of expected results 18.

These analysis activities may result in the detection of a physical attribute of the manufactured object. This physical attribute may be a flaw, delamination, void, fracture, fissure, or crack, among others. Early defect detection helps greatly in materials research. Additionally, in an industry like aircraft servicing, early detection of defects could improve safety and prevent a catastrophic failure.

In a similar manner to that described above, the system 10 may also be used for testing a physical feature. These physical features may include number of layers, layer thickness, fiber number, fiber orientation, and porosity, to name but a few. Testing materials for physical features helps in materials research and for industry. The development of materials customized for specific applications will lead to improved safety, better product quality, and lower cost products.

For testing, the system 10 measures the sonic energy signal 20 indicative of the physical feature. The sonic energy signal 20 may be induced in several ways. It may be induced by a transducer-induced ultrasound technique, a plasma-induced ultrasound technique or a laser ultrasound technique, among others.

Similar to detection, in testing, the sonic energy signal 20 is measured by the measurement system 12. The signal analyzer 16 compares the signal from the measurement system 12 to the expected result 18.

The sonic energy signal 20 may be measured in one of several ways. For example the sonic energy signal 20 may be measured by one or more piezoelectric transducers, one or more electromagnetic transducers, a laser interferometer, or a gas-coupled laser acoustic detector, to name but a few.

The expected result 18 may be the outcome of a previous test of the same object. Alternatively, this result may be the output from a predictive propagation model, an automated expert system, results of a previous test of a similar object, or a set of parameters sought by an expert, among others. The parameters may represent an amplitude setting, a location in a time series graph, a frequency in a frequency domain transformation, or others. Further, the expect result 18 may be test results of a know test model or a known imperfect object. In addition, the expected result 18 may the output of a model. Further, the model may be iteratively adapted to approximate the signal. As a result, parameters of the model may be indicative of the physical attribute of the manufactured object.

This system may be used to test, measure and detect physical features and attributes. For example, the system may be used to detect a flaw or void, among others. The system may also be used to measure a layer thickness, fiber orientation, or porosity.

Figure 2:
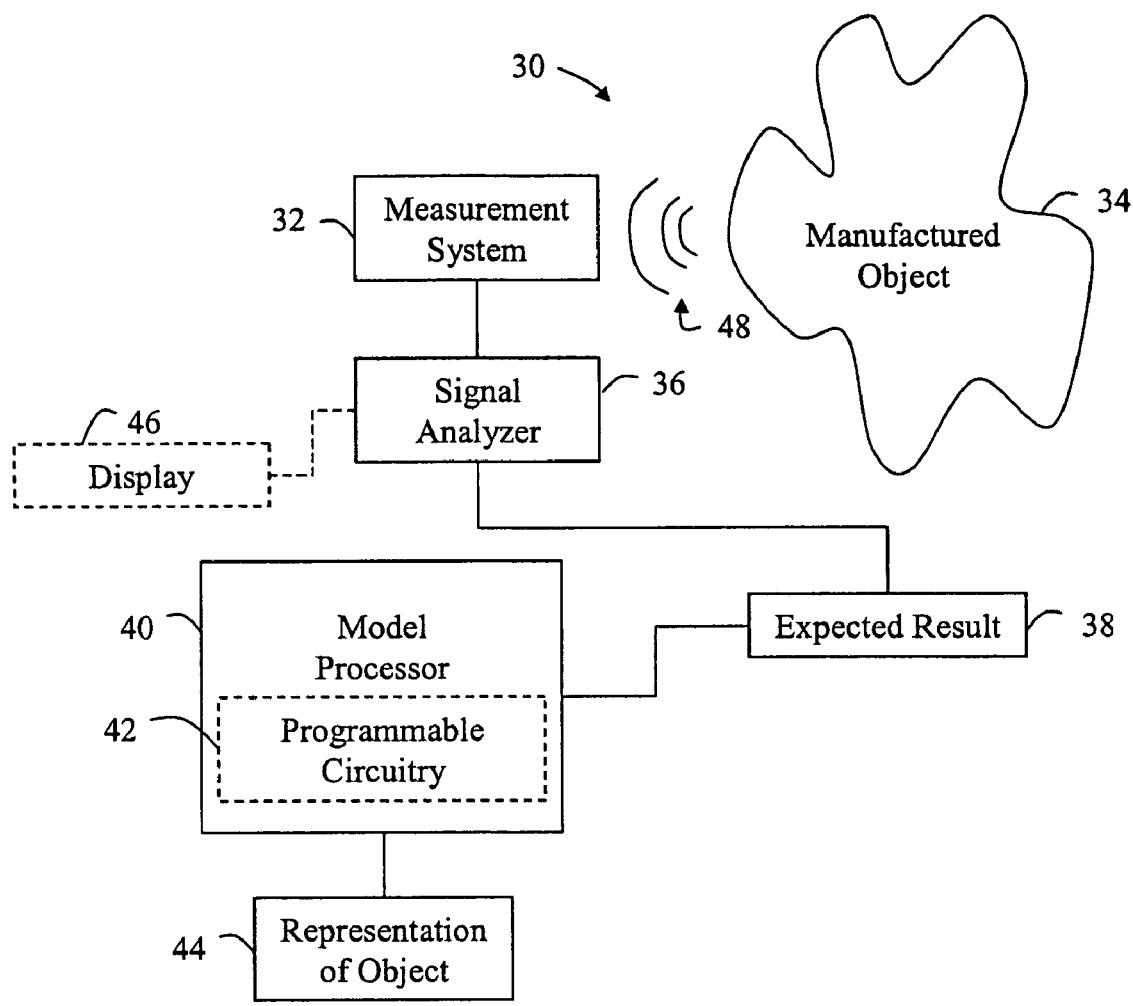
FIG. 2 is a schematic block diagram of an exemplary embodiment of the system of FIG. 1.

FIG. 2 is a schematic block diagram of an exemplary embodiment of the system of FIG. 1. A system 30 for detecting physical attributes of a manufactured object 34 has a measurement system 32, a signal analyzer 36, and an expect result 38, as found in the system of FIG. 1. In addition, the system 30 of FIG. 2 may have a model processor 40, a programmable circuitry 42, a representation of the manufactured object 44, and a display 46.

Similar to the system of FIG. 1, the measurement system 32 communicates with the signal analyzer 36. The expected result 38 is coupled to the signal analyzer 36. As shown, the model processor 40 may be coupled to the expected result 38. However, the model processor 40 may communicate directly with the signal analyzer 36.

The representation of the manufactured object 44 is accessible to the model processor 40. This may be accomplished as a computer-aided-drafting representation in a memory storage, data on a network device, a file on drive or a simultaneously generated representation, among others. However, it too may be configured in other ways. For example, the representation of the manufactured object 44 may communicate directly with the programmable circuitry 42.

The programmable circuitry 42 is shown as part of the model processor 40. However, this circuitry may be separate from the model processor 40. The programmable circuitry 42 may provide adaptable functionality to the system. For example, the programmable circuitry 42 may permit models, parameters, and configurations to be interchanged in the system. The programmable circuitry 42 may allow programs and instruction sets to be swapped as desired.

The display 46 may be included to provide a representation of the results of the signal analysis. This display 46 may communicate with the signal analyzer 36. However, it may also communicate with the model processor and/or the expected result, to name a few.

The embodiment of FIG. 2 operates in a similar manner to that of FIG. 1. The measurement system 32 detects an sonic energy signal 48 such as an ultrasound signal. The signal analyzer 36 automatically compares the sonic energy signal 48 to the expected result 38 and produces an analysis result. The analysis result may be represented on the display 46.

For example, an interferometer may measure a sonic energy signal, such as an ultrasound signal. The interferometer may detect distortions in a reflected laser beam. The distortions may be converted to a time domain voltage signal. This voltage signal may be received by a signal analyzer. The signal analyzer may compare the voltage signal to an expected result 38. For example, the expected result 38 may be the output of a wave propagation model.

Additionally, the expect result 38 used in the analysis may be an outcome of a previous test. The result 38 may also be the output of an expert system, the solution to a propagation model, or a set of parameters sought by an expert, to name but a few. The parameters, above, may represent an amplitude setting or a location in a time series graph.

The expected result may be generated by the model processor 40. The model processor 40 may, for example, use a propagation model or expert system, among others, to generate the expected result 38. The model processor may also determine the expected result 38 from a representation of the manufactured object 44. In addition, the model processor 40 may generate the expected result 38 with a programmable circuitry 42.

For example, the model processor 40 in communication with the programmable circuitry 42 may be a computer with software appropriate for generating the results of a propagation model. However, the model processor 40 may also be a computer with an expert system or an analog circuitry, to name a couple alternate examples.

The programmable circuitry 42 may be reprogrammed with a hand held device, over a network, by direct action through a keyboard, or through other means. The outcome is an adaptable circuitry and an adaptable system 30.

The representation of the manufactured object 44 may be found in many forms. These forms may include a computer-aided-drafting representation, a data map associated with the manufactured object, or a set of parameters characteristic of the material, among others. The parameters above may be number of layers, types of material, velocities of sound through different materials, object size, and key dimensions, among others.

The display 46 may also take many forms. These forms may include a monitor on a computer, an oscilloscope, a printer, a television screen, a visual or sonic alarm, or others. The display may be a C-scan, a B-scan or others. Additionally, the display may represent the results of the signal analysis in relation to images of the object. Further, the display may represent the results of the signal analysis in a 3-D representation relative to the geometry of the manufactured object.

Various combinations or connections are imagined. The components may be implemented separately, or in various combinations.

In the manner described above, the system 30 of FIG. 2 can detect a physical feature in a manufactured object or test a manufactured object for physical attributes. As stated above, the detection of a feature like a defect could improve safety and prevent catastrophic failure. This system also accelerates testing and reduces reliance on experts. Ultimately, the method reduces the cost, making testing more practical. Lower cost testing will lead to broader application in materials research and service safety inspections. As a result, this system could have a significant impact on safety and performance of high cost products like airplanes and automobiles.

Figure 3:
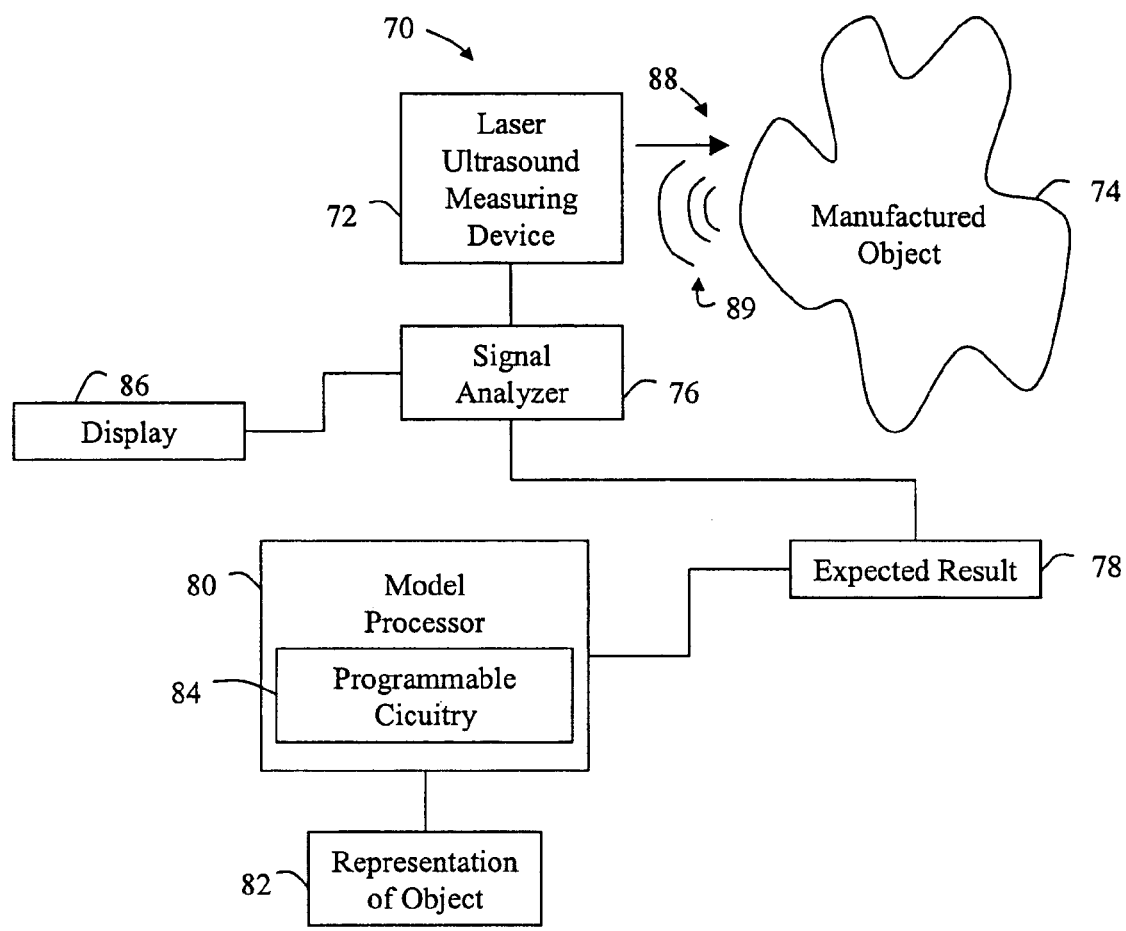
FIG. 3 is a schematic block diagram of another exemplary embodiment of the system of FIG. 1.

FIG. 3 is a schematic block diagram of another exemplary embodiment of the system of FIG. 1. In this embodiment, the system 70 has a laser ultrasound measuring device 72, a signal analyzer 76, an expected result 78, a model processor 80, and a representation of the manufactured object 82. The system 70 may also have a display 86 and a programmable circuitry 84.

As in the systems of FIG. 1 and FIG. 2, a sonic energy signal 89 from the manufactured object 74 is measured by the laser ultrasound measuring device 72. In the embodiment of FIG. 3, the sonic energy signal is initiated by a laser pulse 88. The laser ultrasound measuring device 72 measures the initiated sonic energy signal and produces a measured signal. Then, the signal analyzer 76 automatically compares the measured signal from the laser ultrasound measuring device 72 and the expected result 78. The outcome of the comparison may then be displayed on the display 86.

The expected result 78 may be generated by the model processor 80. This model processor 80 may use a programmable circuitry 84 and/or a representation of the object 82 to generate the expect result 78.

For example, the model processor 80 may be computer. The programmable circuitry 84 may hold software and the representation of the manufactured object 82 may be a computer-aided-design (CAD) representation of the manufactured object. The computer may use a software-encoded ultrasound wave propagation model and the CAD representation of the object to generate an expected propagation wave. However, the model processor 80, programmable circuitry 84, and representation of the manufactured object 82 may take many different forms.

Figure 4:
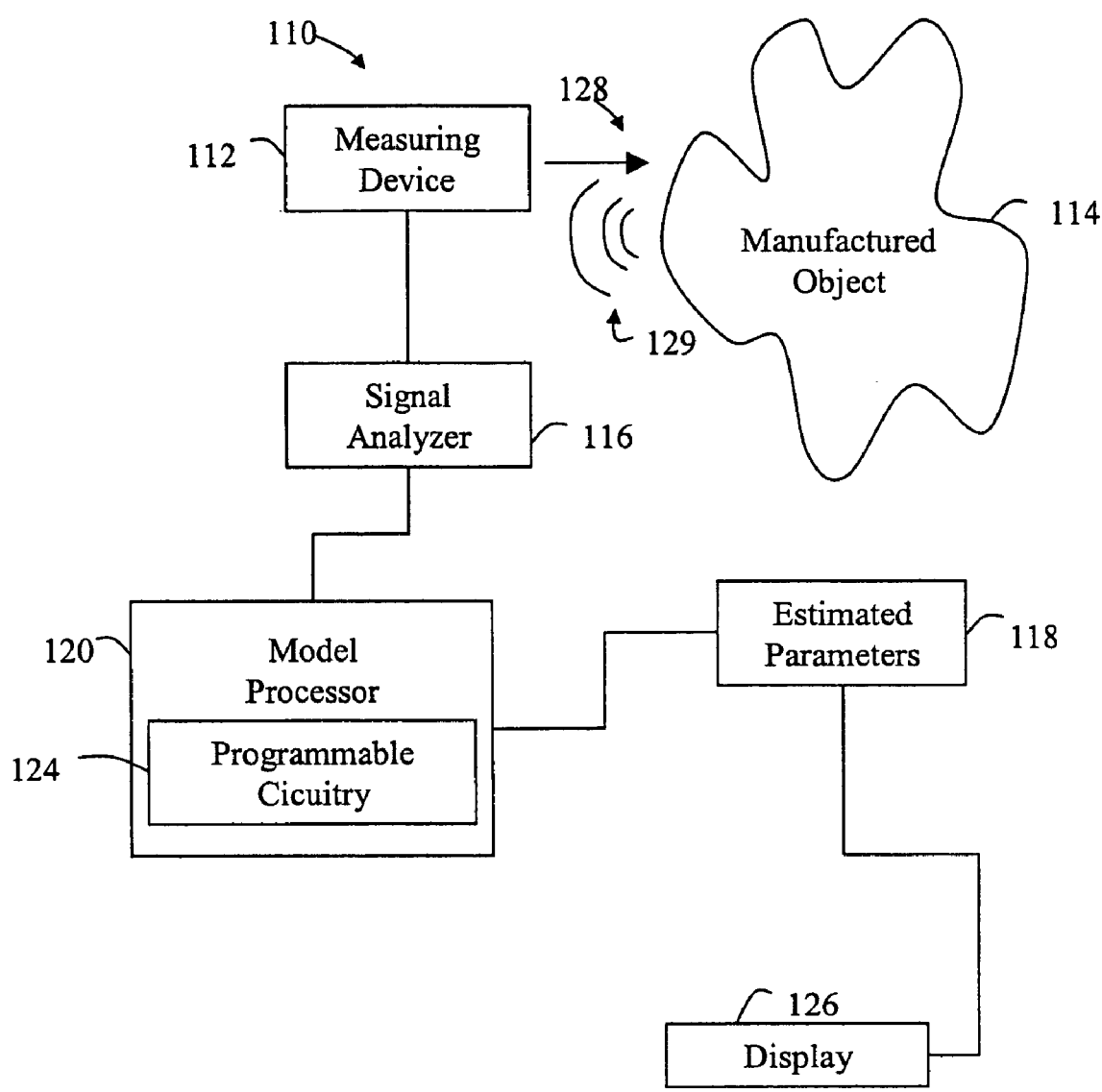
FIG. 4 is a schematic block diagram of another exemplary embodiment of the system of FIG. 1.

FIG. 4 is a schematic block diagram of another exemplary embodiment of the system of FIG. 1. The system 110 has a measuring device 112, a signal analyzer 116, and a model processor 120. The measuring device 112 is connected to the signal analyzer 116. The signal analyzer 116 communicates with the model processor 120.

In addition, one or more estimated parameters 118 are accessible by the model processor 120. Further, these estimated parameters 118 may be displayed on a display 120. The estimated parameters 118 may be accessed by the display 120.

Further, the model processor 120 may have a programmable circuitry 124. The model processor 120 and the programmable circuitry 124 may take many forms, including those forms described above and below, among others.

These elements may be configured as shown. Other elements such as a representation of the manufactured object may also be included. In addition, these and other elements may function in many other configurations. For example, the estimated parameters 118 and the display 126 may be accessible by the signal analyzer 116.

The measuring device 112 may measure a signal 129. A signal generator may be included as needed to generate the signal through interaction 128. However, the signal may be generated through alternate means.

The signal analyzer 116 may then compare the signal to the output from the model processor 120. The model processor 120 may generate an output for comparison. The signal analyzer 116 may direct the model processor 120 to produce the output. Further, the model processor 120 may iteratively produce the output, adapt the output, or change the output in response to a signal from the signal analyzer 116.

In addition, the model processor 120 may use the programmable circuitry 124 to produce, adapt, and/or change the output. Further, the model processor 120 may access the estimated parameters 118 in performing its function. Furthermore, the model processor 120 may access a representation of the manufactured object in determining the output.

For example, the signal analyzer 116 may compare a measured signal to an output from the model processor 120. The signal analyzer 116 may then send a direction and/or output to the model processor 120. The direction may, for example, take the form of a command to iterate or re-determine the output. The output may, for example, take the form of a signal indicating the level of similarity between the measured signal and the output from the model processor 120.

As such, the model processor 120 may, for example, access the estimated parameters 118. Further, the model processor 120 may change the estimated parameters 118. For example, the model processor 120 may adapt parameters in a model used to determine the output. The model may, for example, be a sonic propagation model. The model processor 120 may iteratively change parameters of the model to generate an output approximating the measured signal. As such, the model processor 120 may use and/or change the estimated parameters 118. These estimated parameters 118 may converge to values indicative of the manufactured object. Further, the resulting estimated parameters 118 may be accessed by a display.

Alternatively, the model processor 120 and/or the signal analyzer 116 may compare the measured signal to a set of predetermined outcomes. These outcomes may have associated estimated parameters 118. These outcomes may, for example, be indicative of known physical attributes. For example, a known defect may be characterized by a known signal. The measured signal may be compared to a set of outcomes indicative of flawless, and various types of flaws, among others.

In addition, the parameters 118 may be accessed by the display 126. Further, the display 126 may be accessed and/or may access the signal analyzer 116 and/or the model processor 120.

Figure 5:
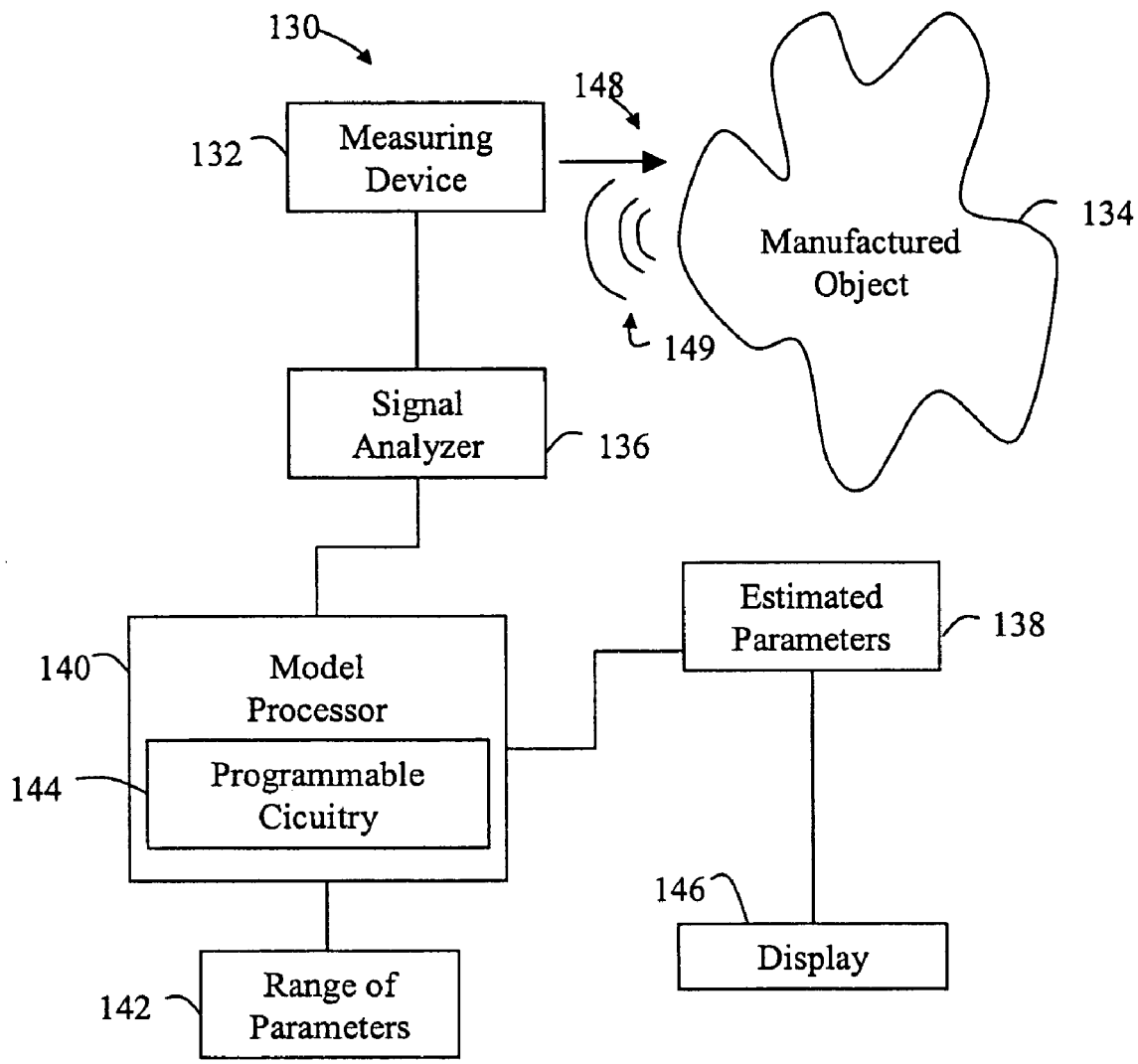
FIG. 5 is a schematic block diagram of a further exemplary embodiment of the system of FIG. 1.

FIG. 5 is a schematic block diagram of a further exemplary embodiment of the system of FIG. 1. The system 130 has many of the same elements of the system described in FIG. 4. These elements may be in the configuration shown in FIG. 4 and/or in FIG. 5. Alternatively, these elements may configured in various ways.

In the exemplary embodiment of FIG. 5, a range of parameters 142 is depicted. This range of parameters 142 may be accessed by the model processor 120. However, it may also be accessed by the signal analyzer 136 and/or the display 146.

In this exemplary embodiment, the system 130 may function to iteratively determine estimated parameters 138 as described above. Further, a set of outputs may be compared to the measured signal to determine the estimated parameters 138.

These estimated parameters 138 may be compared to the range of parameters 142 or an expected parameter. This comparison may be performed by the model processor 120 and/or the signal analyzer 136. Further the comparison may be accessed by the display 146.

This comparison may be indicative of the manufactured object. For example, if the estimated parameters 138 are within the range of parameters 142 or match the expected parameter, the manufactured object may, for example, meet tolerance ranges set for quality control. However, these ranges may alternatively indicate a flaw, type of flaw, a physical attribute, or others. For example, the range of parameters 142 may be indicative of a void, a number of layers, a fraction of fibers, and others.

Figure 6:
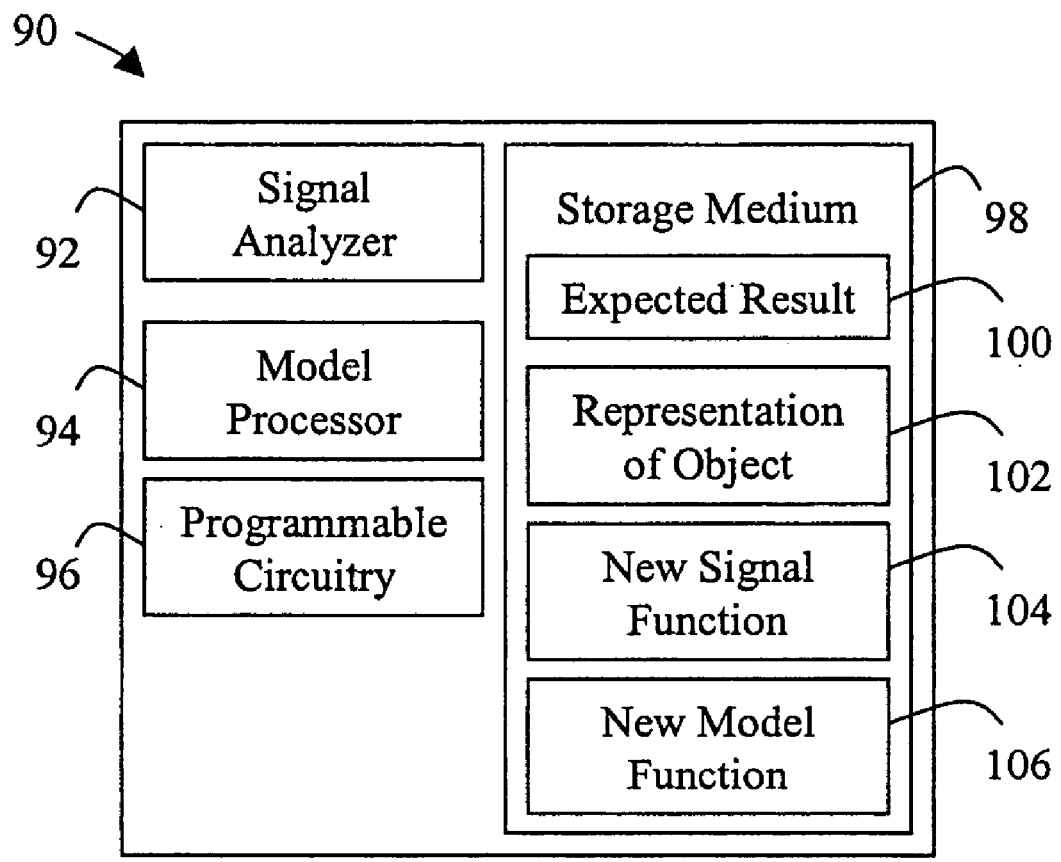
FIG. 6 is a block schematic diagram detailing how components of FIG. 1 may be implemented.

FIG. 6 is a block schematic diagram detailing how components of FIG. 1 may be implemented. A signal analyzer 92 and a model processor 94 may be implemented on the same device 90. A programmable circuitry 96 may also be implemented on the device 90. In addition, a storage medium 98 may be contained in the device 90. The storage medium 98 may hold an expected result 100, a representation of a manufactured object 102, a new signal function 104, and a new model function 106. Further, the storage medium 98 may hold an estimated parameter.

The signal analyzer 92, model processor 94, and programmable circuitry 96 may function as described in FIG. 1, FIG. 2, and FIG. 3. Similarly, the expected result 100 and the representation of the manufactured object 102 may take the forms described above. The new signal 104 may replace or change the signal analyzer's 92 method of operation. Further, the new model function 106 may replace or change the model processor's 94 method of operation. The new model function 106 may also replace the model and model parameters used by the model processor 94.

An exemplary embodiment consistent with the description above is a computer with a microprocessor and a memory. Software on the computer would perform the functions of the signal analyzer 92 and the model processor 94. The software would access the expected result 100 and the representation of the manufactured object 102 to perform the functions. Further, the software may change the signal analyzer's 92 function and the model processor's 94 function by accessing the new signal function 104 and the new model function 106, respectively.

This example is intended to illustrate one possible embodiment of the invention, among others. Therefore, the invention is not limited to this example. Each of the items listed may be housed together, separately or in any combination. Each item may also be included on an as needed basis.

Figure 7:
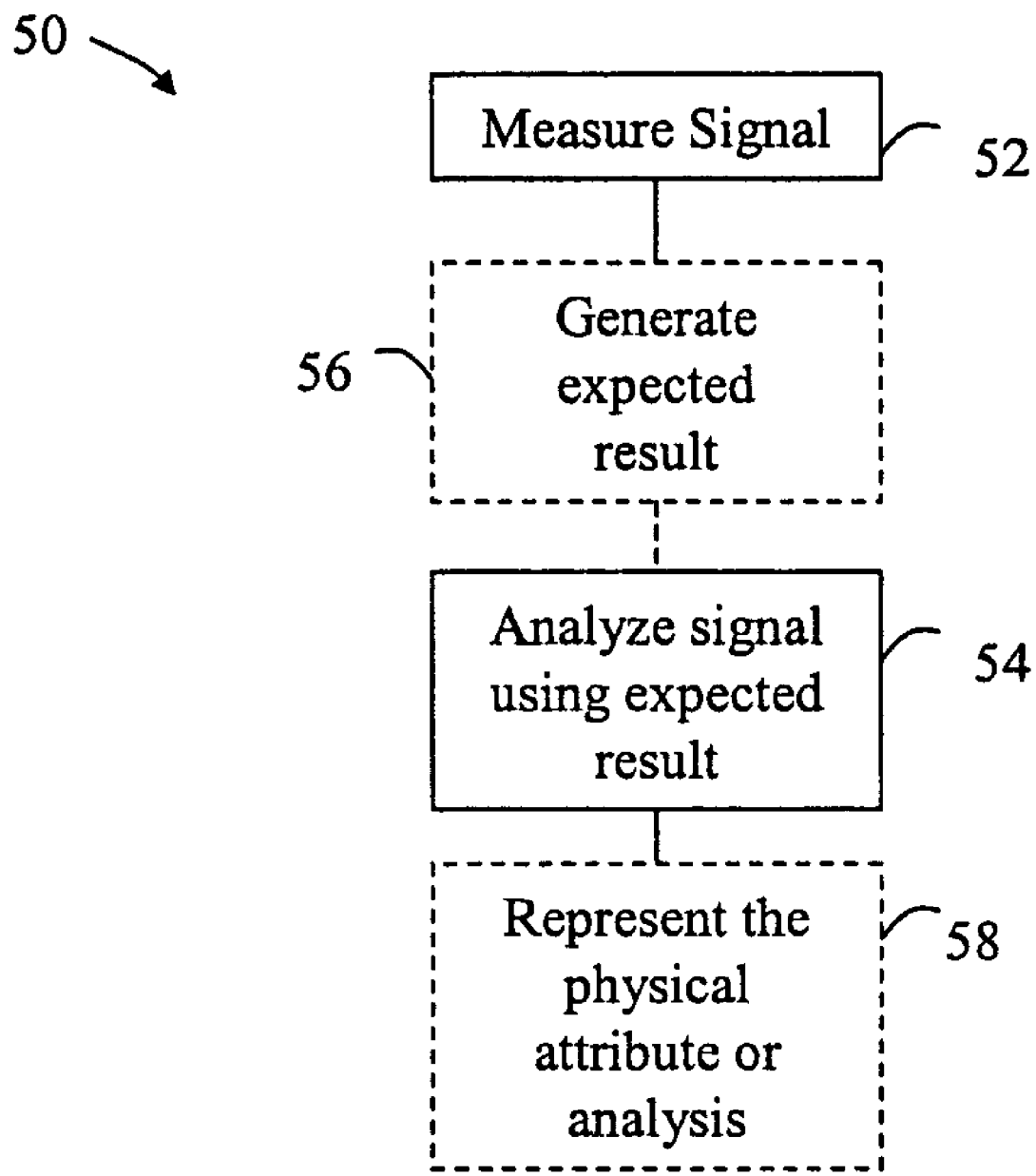
FIG. 7 is a block flow diagram of an exemplary method which may be used by the systems of FIGS. 1, 2, and 3.

FIG. 7 is a block flow diagram of an exemplary method which may be used by the systems of FIG. 1, FIG. 2 and FIG. 3. In a block 52, a sonic energy signal is measured from the manufactured object. In a subsequent block 54, the signal is analyzed by comparing the signal to an expected result. As seen in block 56, this expected result may be generated or previously generated and accessed here. In the next block 58, the result of the comparison or the physical attribute detected through the comparison may be represented on a display.

As described in the systems of FIG. 1, FIG. 2 and FIG. 3, the signal measurement may utilize various techniques. These techniques may include one or more piezoelectric transducers, one or more electromagnetic transducers, a laser interferometer, or a gas-coupled laser acoustic detector, to name but a few.

The step of analyzing the signal may be accomplished by manipulating the signal and expected result in several ways. These manipulations may include a simple subtraction of the expected result from the signal, transformation of the time domain signal into a frequency domain, or filtering the signal, among others. The analysis of the signal may also be performed by an expert system picking relevant amplitude peaks in the signal. Further, the analysis may include comparisons between a frequency domain transformation of the signal and the expected result. Additionally, the analysis may identify peaks, measure time differences between peaks, or watch for missing peaks, to name but a few analysis activities. The result of the analysis may be the detection of a physical attribute or a comparison of the signal and the expected result.

As above, the expected result may be a stored result or it may be generated. The generation of the expected result may be performed prior to the analysis of the signal or in parallel with the signal analysis. The generation step may be accomplished through several means such as using a model processor. For example, the model processor may use a propagation model or expert system, among others, to generate the expected result. The model processor may also determine the expected result from a representation of the manufactured object.

In a further block 58, the result of analyzing the signal may be represented and/or displayed. The physical attribute or the analysis may be displayed using several methods. For example, these methods may include a monitor on a computer, an oscilloscope, a printer, a visual or sonic alarm, a television screen, or others.

Using a method similar to the method of FIG. 7, the benefits of the systems above may be realized. As a result, products with greater safety and higher quality will be made available at lower costs.

Figure 8:
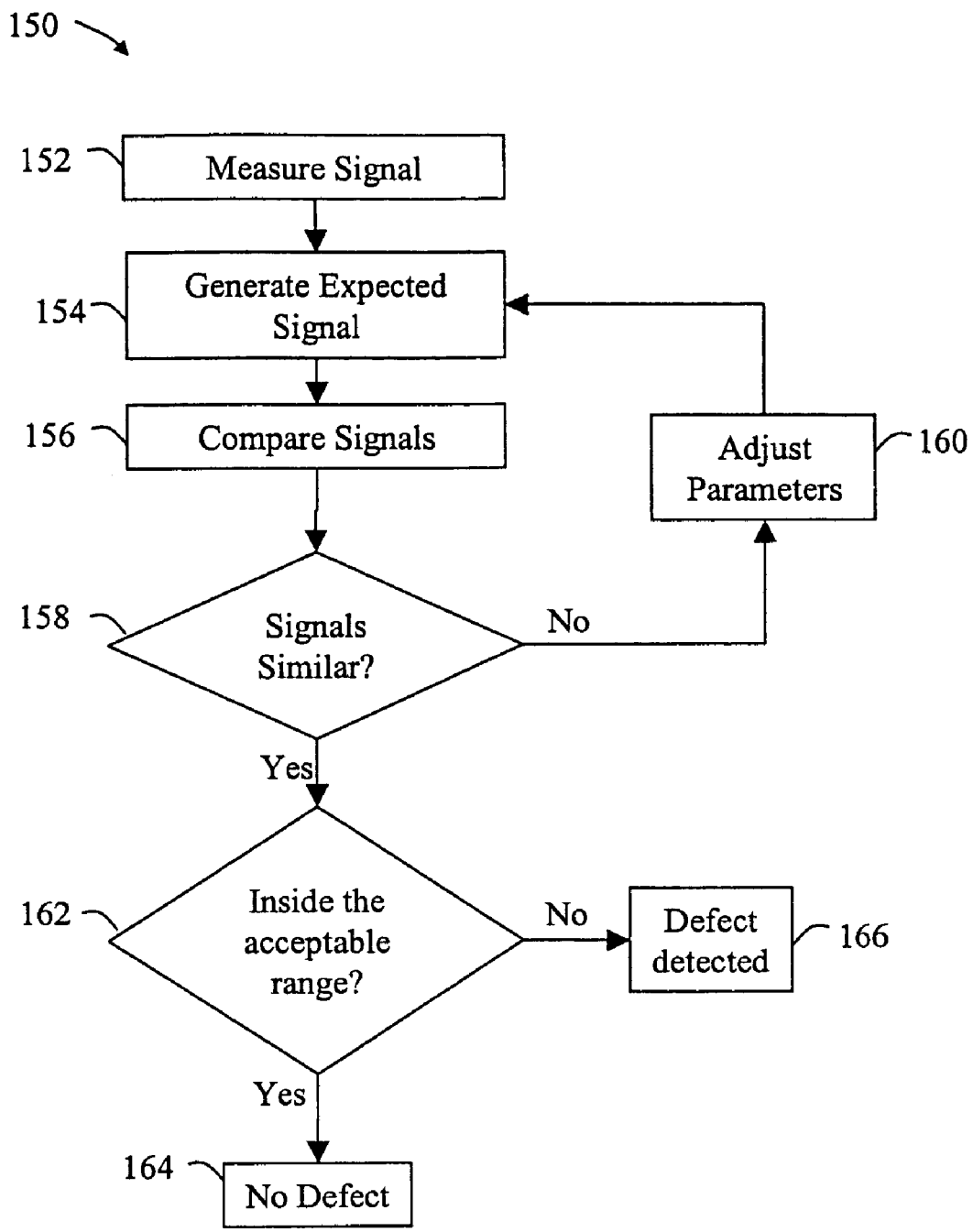
FIG. 8 is a block flow diagram of an exemplary method which may be used by the systems of FIGS. 4, and 5.

FIG. 8 is a block flow diagram of an exemplary method which may be used by the systems of FIGS. 4, and 5. In the method 150, a signal is measured as depicted in a block 152. In a block 154, the expected signal is generated. The expected signal may be generated sequential to the measurement, in coincidence with the measurement, and before the measurement, among others. Further, the expected signal may be a single expected output, the first in an iterative set of model outputs, one of a predetermined set of output, or others.

The measured signal and the expected signal may the be compared as shown in a block 156. In the case of an iterative model or comparison with a predetermined set, the comparison may yield an indication as to whether the signals are similar. This indication may, for example, by a measure of difference such as a mean square difference, a comparison of peak amplitudes, a comparison of features, and others. However, the comparison may take various forms and should not be limited by the examples.

If the signals are not similar, a new parameter may be determined as shown in a block 160. Alternatively, a new predetermined output may be selected. The expected signal may be generated again and selectively compared in an iterative manner. The system may keep track of the number of iterations. After a predetermined number of iterations, the model might be considered as unable to generate an expected signal considered as similar to the experimental signal, a defect is flagged.

If the signals are similar, the parameters may be compared to a range of parameters. If the adjusted parameters or, alternately, those of the selected predetermined output are within the range of parameters, the manufactured object may be within quality tolerances, for example. However, the range may be indicative of a flaw, a type of flaw, lack of a flaw, a physical attribute, and others.

Further, the process may be selectively repeated for various regions about a manufactured object. The term "about" may mean in, on, or in proximity to. For example, the manufactured object may be tested by measuring a sonic signal from various regions of the manufactured object. The method above may be repeated for each and/or selected regions.

Figure 9:
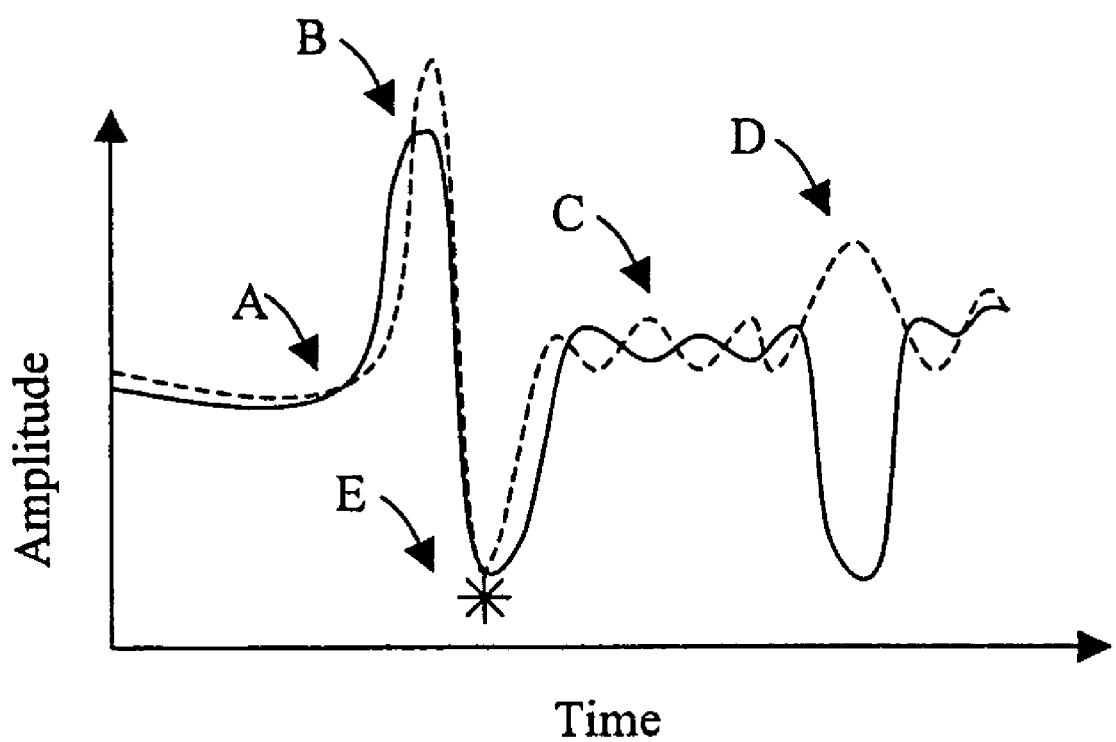
FIG. 9 is a time series graph of a exemplary comparison between an expected result and a signal as recited in the method of FIG. 4.

FIG. 9 is a time series graph of an exemplary comparison between an expected result and a signal as recited in the method of FIGS. 7 and/or 8. The solid line represents a measured signal. The dashed line represents an expected result. The star may also represent an expected result where the expected result is simply an expected peak location and amplitude.

The signal may be initiated by the means described above. These means may include a transducer, a laser pulse, or a plasma pulse, among others. The signal may also be measured by methods recited above. These methods may be one or more transducers, a laser interferometer, or a gas-coupled laser acoustic detector, to name a few.

As previously described, the expected result may be one of a previous measurement, a result of a mathematical model, an expert system, or others. In FIG. 9, the result is shown as either a previous measurement or a result of an ultrasound generation and propagation model. However, the expected result is not limited by these examples and may take other forms.

In FIG. 9, the dashed and solid lines show several interactions that may indicate a physical attribute. For example, at a point A, the expected result and signal meet and begin a rise to a peak. Differences in the beginning of the rise in the signal and that in the expected result may be indicative of several features. For example, the offsets in beginning time may indicate differing layer thickness between that used by a propagation model and the actual material. The absence of an expected peak may indicate a void between layers.

At a point B, both the expected result and the signal reach a maximum amplitude or peak. At this peak, the expected result has a higher amplitude than the signal. This disparity between peak amplitudes may be indicative of incorrect predictions about acoustic properties.

At another point C, the expect result and the signal both oscillate. However, they may oscillate with differing periods, amplitudes, and phase angles. For example, differing oscillations may indicate the existence of a small layer, such as an epoxy layer, between two larger layers. The small layer may not have been included in the propagation model from which the expected result was derived.

The expected result may also predict an inverse wave or no wave where the signal shows one to exist. For example, at point D, the expected result predicts a small amplitude positive wave and the signal shows a large amplitude negative wave. The situation may also be reversed where the signal shows the small amplitude positive wave and the expected result predicts a large amplitude negative wave. In this example, an unanticipated layer, such as an epoxy layer, may cause a difference in the expected results and the signal.

In addition, the expected result may take another form. For example, the expected result may be an expected peak amplitude and location as indicated by another point E. A comparison may be a least squares difference between the signal and the expected point E, a determination as to whether the peak crossed the amplitude of the expected point E, a test to determine whether the peak occurred before or after the expected point E, or others.

If comparisons similar to the examples above were performed automatically during testing, defects would be detected consistently and without the labor of an expert. Tests would be performed faster and with less expense. Lower cost would make flaw detection more economical for use in safety inspections and material testing. As a result, the system and method recited above would lead to greater safety and may prevent catastrophic accidents.

The points described above are presented for illustrative purposes. Many possible comparisons may be performed between measured signals and results from propagation models. Also, the explanations of the phenomena presented above are not necessarily indicated by those phenomena nor are the phenomena exclusive to the physical features mentioned in the examples. All, some, or none of the phenomena may be seen in any given comparison between measured sonic signals and expected results.

Figure 10:
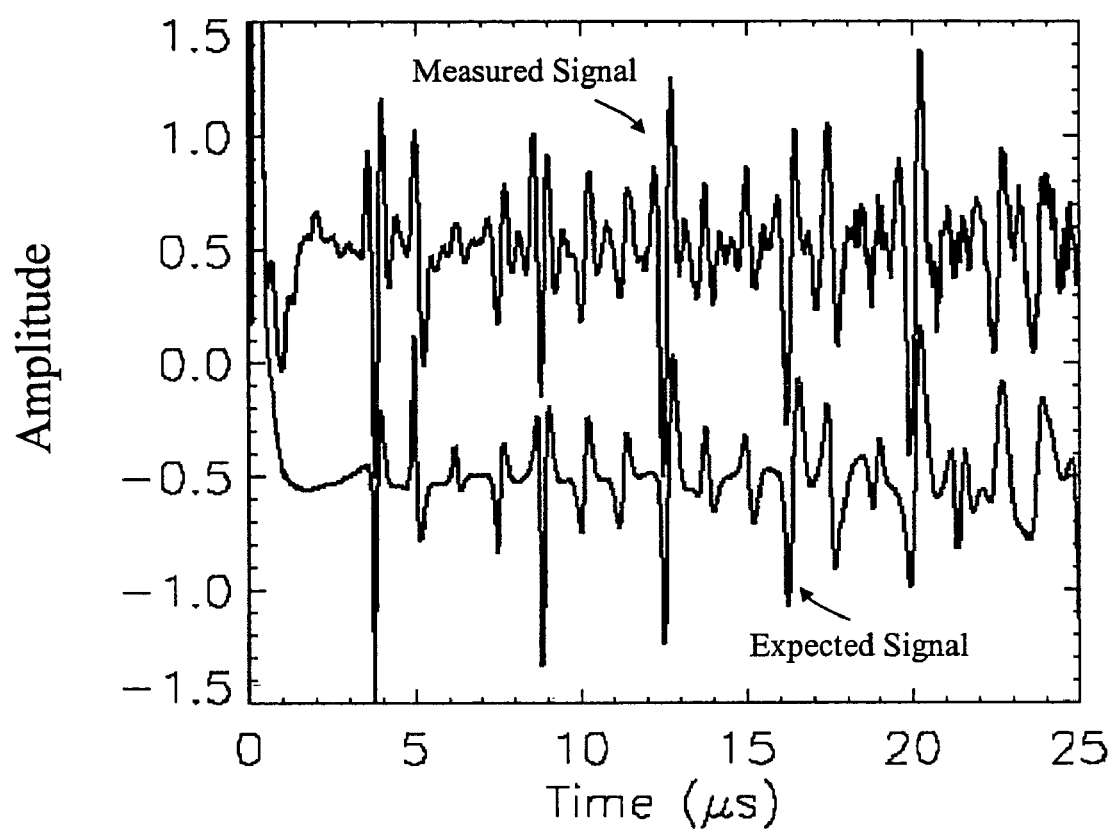
FIG. 10 is a time series graph of a exemplary comparison between an expected result and an experimental signal from a multi-layer sample without defect as may result from the methods of FIGS. 7 and 8.

FIG. 10 is a time series graph of a exemplary comparison between an expected result and an experimental signal from a multi-layer sample without defect as may result from the methods of FIGS. 7 and 8. A comparison may, for example, be made between the two signals.

For example, the lack of a flaw may be determined by a comparison of features. Further, the location of the features in time and/or the amplitude of the features may be indicative of the object. For example, the expected signal may be a predetermined signal generated by a model. Alternatively, the expected signal may be previous measurement of the manufactured object or a known sample of a similar manufactured object. The comparison may indicate the lack of a flaw In addition, the expected signal may be the result of a model. The model parameters may be iteratively and/or adaptively adjusted in order that the expected result approximate the measured signal. The model parameters used to determine the expected result may be indicative the manufactured object. If these parameters are within a given range, the manufactured object may, for example, pass a quality test.

Further, the comparison of the signals may yield information as to the physical attribute and/or features of the manufactured object. For example, the number of layers, the thickness of layers, the orientation of fiber, and others may be determined through the comparison.

Furthermore, the comparison may be quantified through many techniques. These techniques may include a difference, a comparison of feature amplitudes, a mean square difference, a least square difference, an maximum difference, and others.

However, the expected signal may be determined from many sources. Further, FIG. 10 is an exemplary time series graph. The comparison may be performed using other graph types and other methods.

Figure 11:
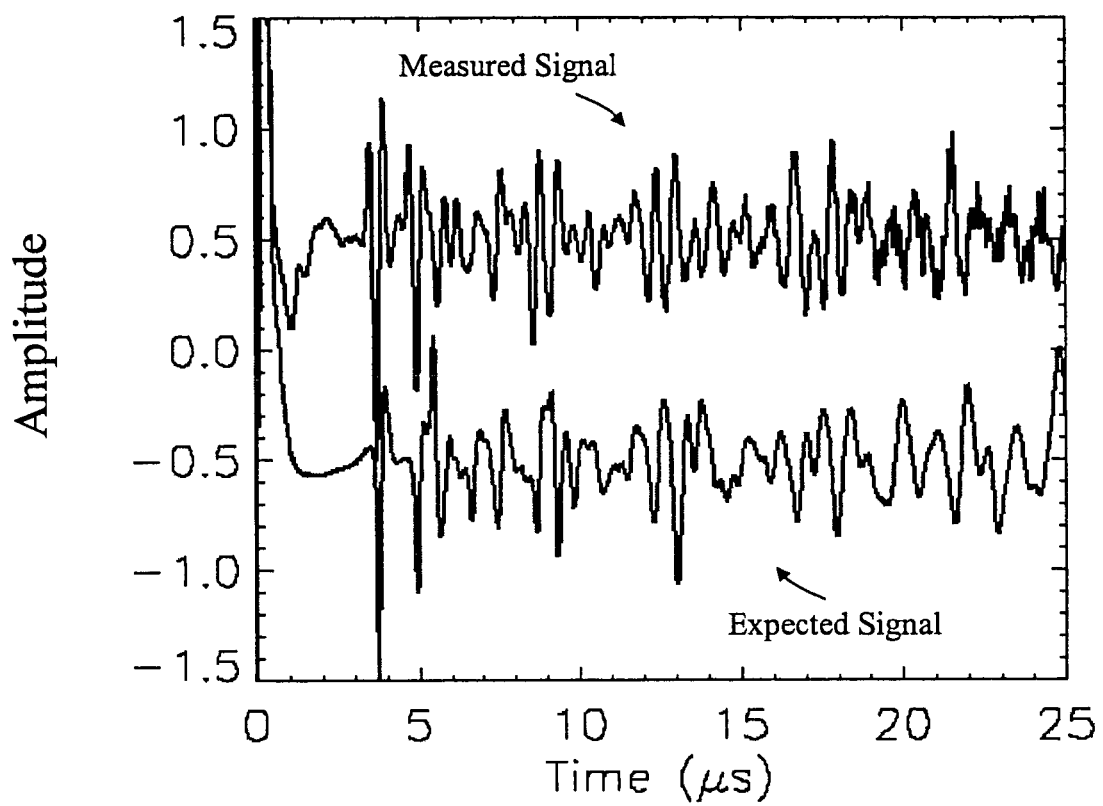
FIG. 11 is a time series graph of a exemplary comparison between an expected result and an experimental signal from a multi-layer sample with a defect as may result from the methods of FIGS. 7 and 8.

FIG. 11 is a time series graph of a exemplary comparison between an expected result and an experimental signal from a multi-layer sample with a defect as may result from the methods of FIGS. 7 and 8. A comparison may, for example, be made between the two signals.

For example, the flaw may be determined by a comparison of features. Further, the location of the features in time and/or the amplitude of the features may be indicative of the flaw. For example, the expected signal may be a predetermined signal generated by a model. Alternatively, the expected signal may be a previous measurement of the manufactured object or a known sample of a similar manufactured object with a flaw. The comparison may indicate the type of flaw In addition, the expected signal may be the result of a model. The model parameters may be iteratively and/or adaptively adjusted in order that the expected result approximate the measured signal. The model parameters used to determine the expected result may be indicative the manufactured object with a flaw. If these parameters are within or outside a given range, the manufactured object may, for example, fail a quality test. Further, the range of parameters may indicate the type of defect.

Furthermore, the comparison may be quantified through many techniques. These techniques may include a difference, a comparison of feature amplitudes, a mean square difference, a least square difference, a maximum difference, and others.

However, the expected signal may be determined from many sources. Further, FIG. 10 is an exemplary time series graph. The comparison may be performed using other graph types and other methods.

As such, a system and method for detecting attributes of a manufactured object are described. In view of the above detailed description of the present invention and associated drawings, other modifications and variations will now become apparent to those skilled in the art. It should also be apparent that such other modifications and variations may be effected without departing from the spirit and scope of the present invention as set forth in the claims which follow.

What is claimed is:

1. A method for detecting an internal physical attribute of a manufactured object using an energy measuring device, the method comprising:
   measuring energy reflected from within the manufactured object with the energy measuring device to obtain a measured complex signal indicative of a structural defect within the manufactured object, the internal physical composition of the manufactured object comprising non-homogeneous material;
   comparing the measured signal to an expected result associated with the manufactured object;
   determining the structural defect based on the step of comparing; and
   displaying the determined structural defect.

2. The method of claim 1, wherein the complex measured signal is a complex compilation of reflections, velocity differences, and amplitude changes, the method further comprising: generating the expected result from a mathematical model of ultrasonic propagation and expected characteristics of the manufactured object.

3. The method of claim 1, wherein the non-homogeneous material comprises material having multiple layers, the method further comprising: deriving the expected result from empirical tests.

4. The method of claim 1, the method further comprising: displaying the structural defect in relation to at least one image of the manufactured object.

5. The method of claim 4, wherein the display is a C-scan.

6. The method of claim 4, wherein the display is a B-scan.

7. The method of claim 4, wherein the structural defect is displayed as a three dimensional image positioned relative to geometry of the manufactured object.

8. A system for the detection of an internal physical attribute of a manufactured object, the system comprising:
   a sonic measuring device operable to perform the following operations:
      detecting a complex signal indicative of a structural defect in the manufactured object, the manufactured object comprising a non-homogeneous material, and generating a measured result associated with the signal;
   an expected result; and
   a signal analyzer, communicatively coupled to the sonic measuring device, that is operable to perform the following operations:
      receiving the measured result;
      comparing the expected result to the measured result responsive to receiving the measured result, and
      producing a comparison of the measured result and the expected result.

9. The system of claim 8, further comprising:
   a model processor communicatively coupled to the signal analyzer; and
   the model processor adapted to generate the expected result from a representation of the manufactured object.

10. The system of claim 9, further comprising:
    a programmable circuitry coupled to the model processor; and
    the model processor adapted to generate the expected result with the programmable circuitry.

11. The system of claim 9,
    wherein the non-homogeneous material object comprises material having multiple layers;
    wherein the sonic measuring device comprises at least one of the following: a laser interferometer or a laser acoustic detector;
    wherein the representation of the manufactured object is stored on a readable medium, the readable medium being communicatively coupled to the model processor; and
    wherein the model processor is operable to perform the operation of generating the expected result from the stored representation of the manufactured object.

12. A system for comparing measurements from an ultrasound testing system, the ultrasound testing system testing a manufactured object for internal physical characteristics and detecting a signal generated on or in the manufactured object, the system comprising:
    a signal analyzer that compares a predetermined expected result with a measured result to determine an internal structural defect in the non manufactured object;
    the manufactured object comprising a non-homogeneous material having multiple layers;
    the measured result associated with the signal detected by the ultrasound testing system; and
    the predetermined expected result associated with the manufactured object.

13. A method for detecting an internal physical attribute of a manufactured object using a sonic measuring device, the sonic measuring device operable to perform the operation of measuring sonic energy from the manufactured object and obtaining a measured signal, the method comprising:
    comparing the measured signal to an expected result to detect an internal physical attribute of the manufactured object, the manufactured object comprising non-homogeneous material, the expected result derived from a model or representation of the manufactured object;
    determining the internal physical attribute based on the step of comparing; and
    displaying information associated with the internal physical attribute.

14. The method of claim 13,
    wherein the manufactured non-homogeneous material comprises having multiple layers; and
    wherein the comparison is selectively repeated, the expected result being repeatedly generated from an iteratively adapted mathematical model, the comparison being selectively repeated until a quantifier indicative of the, comparison has a predetermined value.

15. The method of claim 13, the method further comprising: deriving the expected result from empirical tests.

16. The method of claim 13 wherein the comparison is selectively repeated, the expected result being selected from a set of predetermined expected results, the comparison being selectively repeated until a quantifier indicative of the comparison has a predetermined value.

17. A system for the detection of an internal physical attribute of a manufactured object, the system comprising:
    a signal analyzer communicatively coupled to a sonic measuring device and operable to receive a measured signal, wherein the sonic measuring device comprises a laser interferometer or laser acoustic detector that measures sonic energy from the manufactured object and produces the measured signal;
    an expected result of the manufactured object;
    the signal analyzer operable to perform the following operations:
       comparing the expected result to the measured result automatically to detect an internal physical attribute, and producing a comparison of the measured signal and the expected result.

18. The system of claim 17, further comprising:
a model processor communicatively coupled to the signal analyzer, and
the model processor adapted to generate the expected result from a representation of the manufactured object.

19. The system of claim 18, wherein the representation of the manufactured object is a computer-aided-drafting representation of the manufactured object.

20. The system of claim 18, further comprising:
a programmable circuitry communicatively coupled to the model processor; and
the model processor adapted to generate the expected result with the programmable circuitry.

21. The system of claim 18, wherein the representation of the manufactured object is stored on a readable medium, the readable medium being communicatively coupled to the model processor and the model processor generating the expected result from the stored representation of the manufactured object.

22. The system of claim 17, further comprising:
a display communicatively coupled to the signal analyzer; and
the display adapted to display the comparison of the measured signal and the expected result.

23. A system for the detection of an internal physical attribute of a manufactured object comprising non-homogeneous material, wherein a sonic measuring device measures a sonic energy from the manufactured object and produces a measured signal, the system comprising:
a signal analyzer communicatively coupled to the sonic measuring device and operable to receive the measured signal;
a model processor communicatively coupled to the signal analyzer to provide an output indicative of an expected result of the manufactured object; and
the signal analyzer operable to perform the operations of:
comparing an output of the model processor to the measured result automatically to detect an undesirable internal physical attribute, and
producing a comparison of the measured signal and the output of the model processor.

24. A method for detecting an internal physical attribute of a manufactured object comprising non-homogeneous material, wherein a sonic measuring device measures a sonic energy from the manufactured object and produces a measured signal, the method comprising:
comparing the measured signal to an output from a model processor with a signal analyzer to detect an internal physical attribute, the output indicative of an expected result of the manufactured object;
producing an output from the signal analyzer indicative of the step of comparing; and
displaying the output from the signal analyzer.

25. The method of claim 24, wherein the steps of comparing and producing are selectively repeated, the comparing being of the measured signal and the output from the model processor, the model processor selectively changing the output in response to the output from the signal analyzer.

26. The method of claim 25, wherein the model processor selectively changes the output to one of a plurality of predetermined outputs.

27. A program storage device readable by a machine, tangibly embodying a program of instructions executable by the machine to perform the method steps for detecting an internal physical attribute of a manufactured object using a sonic measuring device, the internal physical composition of the manufactured object comprising non-homogeneous material, the sonic measuring device measuring sonic energy from the manufactured object and obtaining a measured complex signal, said method steps comprising:
comparing the measured complex signal indicative of a structural defect within the manufactured object comprising non-homogeneous material to an expected result;
determining the structural defect based on the step of comparing; and
displaying information associated with the structural defect.

* * * * *